(12) United States Patent
Mullaney et al.

(10) Patent No.: US 8,187,308 B2
(45) Date of Patent: May 29, 2012

(54) INTERNAL JOINT DISTRACTION METHOD

(75) Inventors: Michael W. Mullaney, Kinnelon, NJ (US); Dror Paley, Owing Mills, MD (US)

(73) Assignee: Sixfix Inc., Memphis, TN (US)

( * ) Notice: Subject to any disclaimer, the term of this patent is extended or adjusted under 35 U.S.C. 154(b) by 260 days.

(21) Appl. No.: 12/470,149

(22) Filed: May 21, 2009

(65) Prior Publication Data
US 2009/0234462 A1  Sep. 17, 2009

Related U.S. Application Data

(62) Division of application No. 12/394,590, filed on Feb. 27, 2009.

(60) Provisional application No. 61/067,687, filed on Feb. 29, 2008.

(51) Int. Cl.
*A61B 17/88* (2006.01)
*A61B 17/80* (2006.01)

(52) U.S. Cl. ........................... 606/281; 606/286

(58) Field of Classification Search ............... 606/286, 606/280–282, 57, 60, 90; 623/47, 21.18
See application file for complete search history.

(56) References Cited

U.S. PATENT DOCUMENTS

| | | | | |
|---|---|---|---|---|
| 3,554,193 | A | * | 1/1971 | Konstantinou et al. ......... 606/65 |
| 4,388,921 | A | * | 6/1983 | Sutter et al. ........................ 606/71 |
| 4,693,722 | A | * | 9/1987 | Wall ............................. 623/17.17 |
| 4,726,808 | A | * | 2/1988 | Collins ........................ 623/17.17 |
| 4,940,467 | A |   | 7/1990 | Tronzo |
| 4,968,316 | A | * | 11/1990 | Hergenroeder .................. 606/90 |
| 5,722,976 | A | * | 3/1998 | Brown ............................. 606/281 |
| 6,491,694 | B1 |   | 12/2002 | Orsak |
| 6,916,323 | B2 | * | 7/2005 | Kitchens ....................... 606/86 R |

(Continued)

FOREIGN PATENT DOCUMENTS
JP 2002065682 A * 3/2002

OTHER PUBLICATIONS

European Patent Office, "Notification of Transmittal of the International Search Report and The Written Opinion of the International Searching Authority, or the Declaration," for PCTUS2009/035506, mailed Jun. 9, 2009, 12 pages.

(Continued)

*Primary Examiner* — Thomas C. Barrett
*Assistant Examiner* — Zade Coley
(74) *Attorney, Agent, or Firm* — Haynes and Boone, LLP (57) ABSTRACT

An internal joint distraction device provides articulation to an articulating bone joint between an upper bone structure and a lower bone structure. The device includes a medial plate shaped to at least partially conform to a medial side of a bone structure of a limb and includes a lateral plate shaped to at least partially conform to a lateral side of a bone structure of a limb. Each of the medial and lateral plates may include a longitudinal length sufficient to extend from the upper bone structure to the lower bone structure thereby spanning at least a portion of the joint. Each plates includes at least one proximal connection feature formed therein for connecting to the upper bone structure and at least one distal connection feature formed therein for connecting to the lower bone structure. An axle extends from one of the connection features on the medial plate to one of the connection features on the lateral plate. The axle extends through one of the upper and lower bone structures in a manner that said one of the upper and lower bone structures pivots about the axle relative to the other of the upper and lower bone structures.

10 Claims, 8 Drawing Sheets

U.S. PATENT DOCUMENTS

| | | | |
|---|---|---|---|
| 7,004,943 B2 | 2/2006 | Ferrante et al. | |
| 2003/0233093 A1* | 12/2003 | Moles et al. | 606/60 |
| 2007/0225715 A1* | 9/2007 | Deffenbaugh et al. | 606/69 |
| 2007/0255280 A1 | 11/2007 | Austin et al. | |
| 2008/0275558 A1* | 11/2008 | Clifford et al. | 623/20.14 |

OTHER PUBLICATIONS

Synthes, "Less Invasive Stabilization System (LISS)," Technical Guide, 2000 Synthes (USA), Printed in U.S.A. GP1634C Oct. 2003 J2892-D, 41 pages.

* cited by examiner

INTERNAL JOINT DISTRACTION METHOD

PRIORITY

This application claims priority to and is a divisional of U.S. patent application Ser. No. 12/394,590, filed Feb. 27, 2009, and claims priority to and the benefit of the filing date of U.S. Provisional Application No. 61/067,687, filed Feb. 29, 2008, both of which are incorporated herein by reference in their entirety.

TECHNICAL FIELD

This disclosure relates in general to an implant for treating a condition of the bone, and more particularly, to an internal joint distraction device.

BACKGROUND

The total joint arthroplasty (TJA) market in the US is estimated to be over $9 billion by 2009. While TJA is a very successful procedure overall, this success is not the same for all joints. Researchers continue to look for opportunities to repair the damaged cartilage instead of replacing the joint. This is especially important in younger, more active patients who may outlive their first total joint implant and require a difficult and typically less successful revision procedure. Today, approximately 30% of US TJA patients are under 60 years old.

Joint distraction or Arthrodiatasis is a procedure that is currently being performed in Osteoarthritis (OA) patients for the ankle, hip, and knee joints with bulky external fixation devices. The current procedure involves inserting multiple pins or wires into the bones on each end of the damaged joint and connecting the pins or wires to an external fixation frame. The joint is then pulled apart (distracted) about 5 mm and held in that position for 2 to 3 months. Multiple peer-reviewed clinical papers report 70% or greater success rate with this procedure in the ankle (see clinical results table and article abstracts).

The arthritic ankle market is estimated to be over 50,000 procedures per year in the US and is growing at a 10% annual rate. Surgical treatment options for the arthritic ankle include ankle arthrodesis, total ankle replacement, and external ankle distraction. Each procedure has limitations and most orthopaedic surgeons agree there is not a good option for ankle arthritis. Some researchers believe this market is severely underserved and more than 375,000 patients suffer from arthritic ankles in the US alone.

Ankle Arthrodesis (Fusion) is the most common surgical treatment option for arthritic ankles with over 40,000 fusion procedures performed per year. Fusion limits the patient's motion and changes the gait pattern, which may lead to arthritis in the adjacent subtalar joint.

Total Ankle Replacement (TAR) is gaining popularity; however, this total joint replacement procedure does not have the same successful clinical outcome of hip and knee replacements. A recent meta-analysis reported 5-year implant survivorship at 78% compared to 96+% with total hip and knee replacements.

Joint Distraction with External Fixation (Arthrodiatasis) is a relatively new technique and is only performed by a small number of institutions. For example, the Ilizarov type ring fixator (mainly S&N and Small Bone Innovations) and the unilateral external fixator (Orthofix) each use external fixation systems for distraction. The procedures involve stretching the joint with an external fixation device and leaving the joint distracted for months while the cartilage heals. These techniques require a very large external frame and have patient drawbacks including discomfort and possible pin tract infections. Further, many total joint surgeons are not trained in the application of external fixation frames and find this procedure intimidating.

The present disclosure overcomes one or more shortcomings in the art.

SUMMARY

The present disclosure is directed to a distraction device that provides articulation to an articulating bone joint between an upper bone structure and a lower bone structure. The device includes a medial plate shaped to at least partially conform to a medial side of a bone structure of a limb and includes a lateral plate shaped to at least partially conform to a lateral side of a bone structure of a limb. Each of the medial and lateral plates may include a longitudinal length sufficient to extend from the upper bone structure to the lower bone structure thereby spanning at least a portion of the joint. Each plates includes at least one proximal connection feature formed therein for connecting to the upper bone structure and at least one distal connection feature formed therein for connecting to the lower bone structure. An axle extends from one of the connection features on the medial plate to one of the connection features on the lateral plate. The axle extends through one of the upper and lower bone structures in a manner that said one of the upper and lower bone structures pivots about the axle relative to the other of the upper and lower bone structures.

In another exemplary aspect, the present disclosure is directed to a distraction device that provides articulation to an articulating bone joint between tibia and fibula bone structures and talus bone structure at an ankle joint. The device includes a tibia plate shaped to at least partially conform to a medial side of the tibia, the tibia plate having a bone interfacing surface and a socket portion shaped to a receive a portion of the tibia adjacent the ankle joint. It also includes a fibula plate shaped to at least partially conform to a lateral side of the fibula. Each of the tibia and fibula plates have a longitudinal length sufficient to extend from the respective tibia and fibula to lie adjacent the talus and accept an axle coaxial with the joint axis when connected in place adjacent to the respective tibia and fibula. Each of the plates having at least one proximal connection passage formed therein for receiving a bone screw configured to connect to the tibia or fibula and at least one distal connection passage formed therein for connecting to the talus. An axle extends from the distal connection feature on the tibia plate to the distal connection feature on the fibula plate. It is arranged to extend through the fibula and the talus, and it includes structural features that prevent relative rotation of the axle relative to the talus while permitting the relative rotation of the axle relative to the tibia and fibula plates.

In another exemplary aspect, the present disclosure is directed to a treatment method for maintaining a first bone structure in a distracted state. The method includes the steps of creating a passage through a first bone structure on a first side of an articulating joint, the passage being formed substantially along the axis of the joint. An axle is inserted through the passage. A first bone plate is implanted in contact with and adjacent to one of a medial and lateral side of a second bone structure. A second bone plate is implanted in contact with and adjacent to the other of the medial and lateral sides of the second bone structure. The axle is connected to both the first and second bone plates to provide articulating movement of the first bone structure about the axle relative to the second bone structure.

In another exemplary aspect, this disclosure is directed to a treatment method for maintaining a first bone structure in a distracted state. It includes creating a first passage through a talus substantially along the axis of the ankle joint and inserting an axle through the first passage. The axle includes structural features that prevent relative rotation of the axle relative to the talus. A fibula bone plate is implanted in contact with and adjacent to the lateral side of the fibula such that a connection feature in the fibula bone plate aligns with the axis of the axle. The axle is connected to the fibula bone plate to provide articulating movement of the talus with the axle relative to the fibula. A tibia bone plate is implanted in contact with and adjacent to the medial side of the tibia such that a connection feature in the tibia bone plate aligns with the axis of the axle. The axle is connected to the tibia bone plate to provide articulating movement of the talus with the axle relative to the tibia. A second passage is created through both the tibia and fibula that aligns with a connection feature on each of the fibula and tibia plates. A pin is implanted through the second passage that connects to both the fibular and tibia bone plates.

Further aspects, forms, embodiments, objects, features, benefits, and advantages of the present invention shall become apparent from the detailed drawings and descriptions provided herein.

DETAILED DESCRIPTION

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The devices and methods disclosed herein are internal ankle distraction devices and procedures instead of external distraction devices. These systems and methods may be minimally invasive, reproducible, and may even be suitable for outpatient procedures. In addition, the internal devices and methods may decrease the operative time, make the procedure easier for joint surgeons to perform, and significantly improve patient comfort. These systems may provide the surgeon with a conservative treatment option and expand the continuum of care for their patients.

These devices preserve the joint function of the ankle, which is one of the compelling advantages of distraction. It preserves options for surgeons instead of leaping to the more extreme treatments of fusing the joint or total joint replacement. If the joint distraction procedure does not relieve the pain, surgeons can later fuse the joint or perform total joint replacements. Even still, the devices disclosed herein may delay or eliminate the need for a fusion or total ankle replacement.

Figure 1:
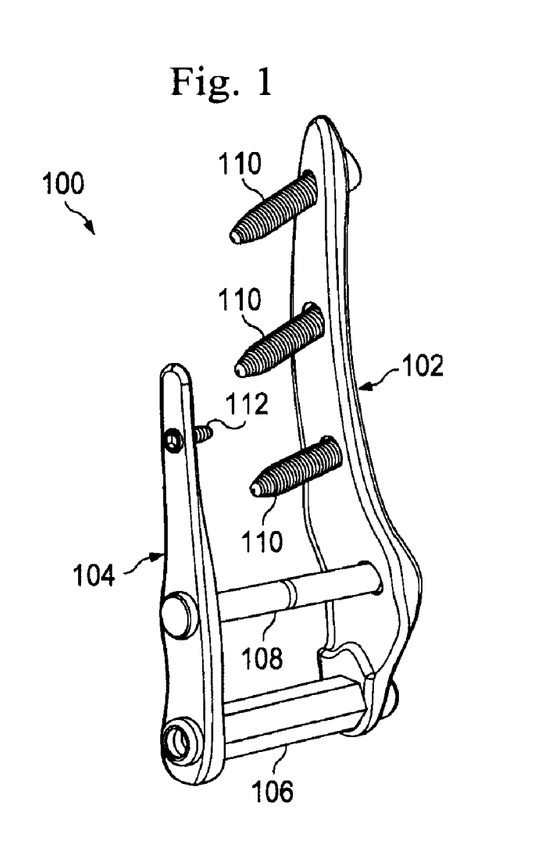
FIG. 1 is an illustration of an isometric view of an exemplary ankle distraction device according to a first aspect.

FIG. 1 shows an exemplary ankle distraction device referenced herein by the numeral 100. Although the devices and methods are described herein with reference to the ankle and its surrounding bone structure, it is contemplated other embodiments may be used for the distraction and support of other joints in a body. The device 100 includes a medial plate 102, a lateral plate 104, an axle 106, and a pin 108. Bone screws 110, 112 are used to secure the medial plate 102 and lateral plate 104 to bone structure on opposing sides of a limb. In the embodiment shown, the medial plate 102 attaches to the tibia and the lateral plate 104 attaches to the fibula. This is further described below.

The medial plate 102 is described in greater detail with reference to FIGS. 2-4 and 5A-5C. Turning to these figures, the medial plate 102 includes an inner facing side 114, an outer facing side 116, a proximal end 118, and a distal end 120. The inner facing side 114 is shaped to interface with bone structure, and in this embodiment, includes an offset bearing surface 126. The bone interfacing portion of surface 114 is shaped to interface with a medial side of a tibia, while the offset bearing surface 126 is located distal to the tibia and receives the axle 106. In some embodiments, the offset bearing surface 126 is part of a cylindrical boss, although other shaped offsets are contemplated.

Figure 2:
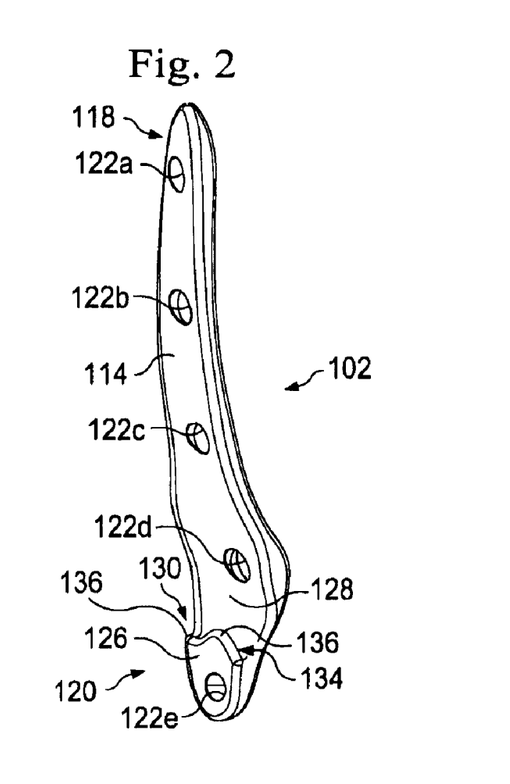
FIGS. 2-4 and 5A-5C are illustrations of an isometric view of an exemplary tibia plate of the ankle distraction device of FIG. 1.
Figure 3:
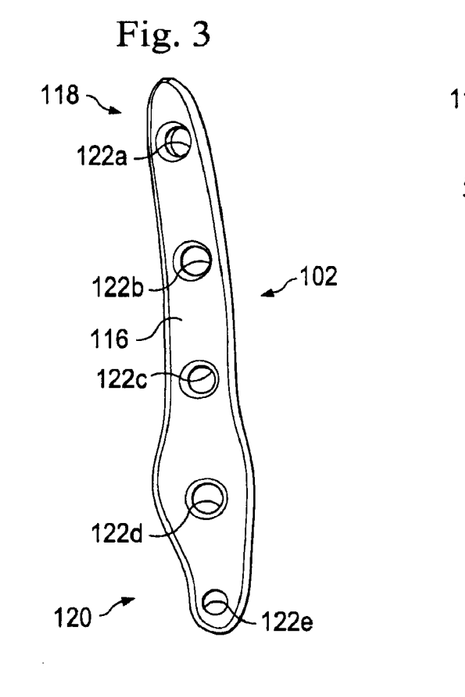
Figure 4:
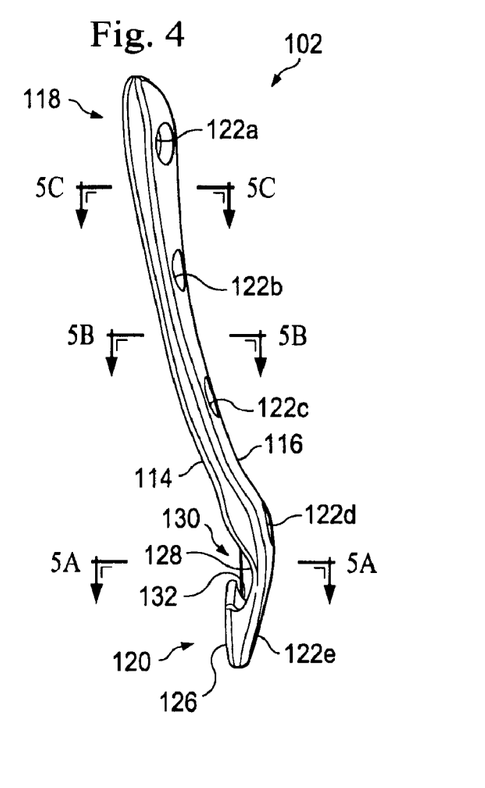

In the embodiment shown, the medial plate includes a plurality of connection features 122a-e formed as holes or apertures for receiving or connecting with one of the axle 106, the pin 108, and the bone screws 110. These connection features 122a-e may be cylindrical bores or may include counterbores or countersinks for receiving heads of screws or features to effect a locking function. Some embodiments include spikes or nails integral with the plates as connection features.

Figure 5A:
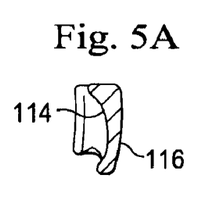
Figure 5B:
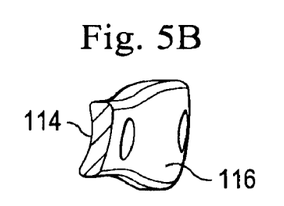
Figure 5C:
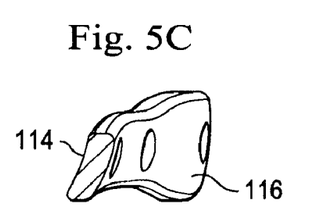

FIGS. 2, 4, and 5A-5C best show the contour of the bone interfacing surface 124 of the inner surface 114. The medial plate 102 extends longitudinally from the proximal end 118 toward the distal end 120. The proximal end 118 has a rounded proximal most edge and a bull-nosed leading edge that accommodates insertion along the bone structure. The inner facing side 114 is contoured to follow the contour of the bone it is adjacent to. For example, near the proximal end 118, and adjacent the connection feature 122a, the inner facing side 114 is relatively flat in cross-section transverse to the longitudinal direction as shown in FIG. 5C. As the distance from the proximal end 118 increases however, the contour of the bone interfacing surface 124 becomes more concave, as shown in FIGS. 5B and 5C, and the width of the plate increases from the proximal end 118 toward a central region or maximum width region.

The distal end 120 of the medial plate 102 includes a spoon-like contour forming a concave socket portion 128. The connection feature 122d is formed within this concave socket portion 128 substantially at or about the deepest portion of the socket portion 128. In addition, shown in FIG. 2, the socket portion 128 is also the widest portion of the medial plate 102. Closer to the distal end 120, the bone interfacing surface 124 transitions to the offset bearing surface 126, in which the connection feature 122e is located. The offset bearing surface 126, like the distal end 120 of the medial plate, also is formed with a relatively concave cross-section.

In addition, as shown in FIG. 4 and FIGS. 5B and 5C, the medial plate profile twists about a longitudinal axis extending in the direction of its longitudinal length for anatomically interfacing with the associated bone structure. The connection feature apertures 122a-e however, are formed in a direction substantially normal to the bone interfacing surface 124 and the offset bearing surface 126. Therefore, axes formed by the connection features 122a-e are not parallel, but are offset at angles relative to each other because of the twisting and curved profile of the medial plate 102. Such non-parallel axes may have increased resistance to pull-out. In addition, the trajectories of the screws may be non-parallel in order to provide similar benefits.

A shoulder 130 between the bone interfacing surface 124 and the offset bearing surface 126 connects the two surfaces. Here, the shoulder 130 is hook-shaped, having a concave seat 132 formed such that, as shown in FIG. 4, the offset bearing surface 126 partially overlaps the bone interfacing surface 124. The concave seat is formed such that a portion of the tibia's proximal end fits within and is supported by the concave seat 132. Accordingly, when properly located on the tibia, the bearing surface 126 is disposed below or extends beyond the tibia while the bone interfacing surface 124 lies adjacent to or substantially in contact with the tibia.

FIG. 3 shows the outer facing side 116. As can be seen, the outer facing side 116 is similar in some respects to the inner facing side, but is primarily convex in cross-section, as shown in FIGS. 5A-C. In the embodiment shown in FIGS. 2-4, where the connection features 122a-e are bores, counter bores or countersinks may be provided that permit the screw heads or nuts to recess into the plates. In some embodiments, the countersinks may be spherical to accommodate spherical screw heads or nuts. In some embodiments, the connection features are spherical bores extending through the whole plate, without a corresponding cylindrical bore. Such spherical surfaces act as seats against which the bone screws 110 may be driven. In some embodiments, locking mechanisms, such as, for example, locking head screws and other systems or methods may lock or secure the screws in place. Furthermore, it is understood that bore configurations other than those explicitly described also could be used. It should be noted that although shown as protruding from the plates, the connection features may be formed so that the screws and all portions of the axle 106 and pin 108 lie flush with or countersunk from the plate surface. This may increase patient comfort and prolong epidermis integrity. The screws used in the device 100, unlike the screws of external type systems, are arranged with a head and a threaded body portion. Because the plates in this system abut against the bone tissue themselves, the screw head is adjacent the threads on the threaded body portion.

Figure 6:
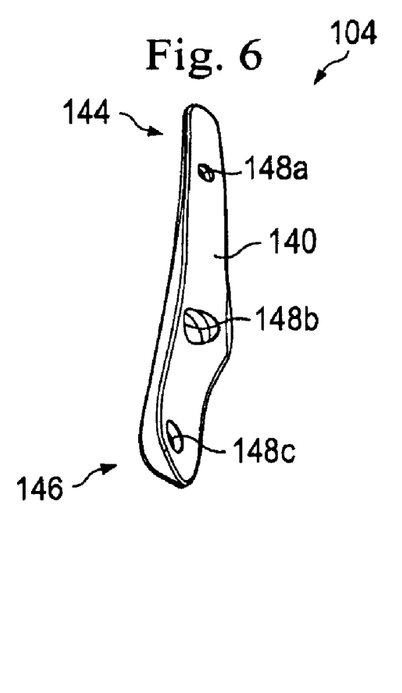
FIGS. 6 and 7 are illustrations of an isometric view of an exemplary fibula plate of the ankle distraction device of FIG. 1.
Figure 7:
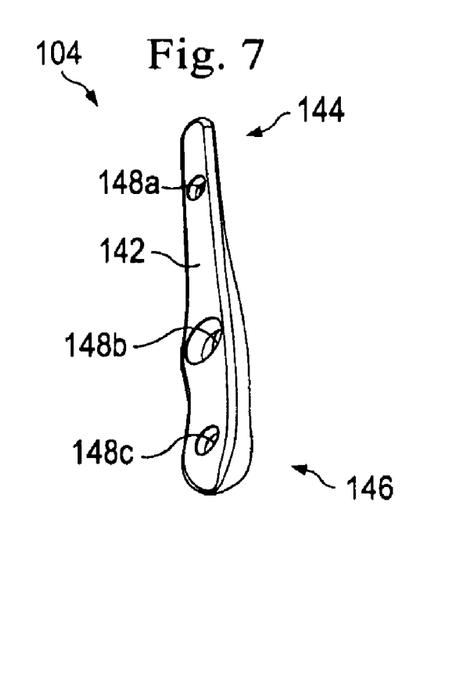

FIGS. 6 and 7 show the lateral plate 104 in more detail. In this embodiment, the lateral plate 104 is structurally shaped and configured to connect with the fibula. It includes an inner facing side 140, an outer facing side 142, a proximal end 144, and a distal end 146. Here, the inner facing side 140 is a concave shape and the outer facing side 142 is flat or generally convex. We note however, that the surfaces need not be concave or convex, but in some embodiments are shaped to match the anatomy of the adjacent bone structure.

Like the medial plate described above, the contour of the concavity changes along the length of the lateral plate 104, with the concavity having a smaller radius and appearing deeper closer to the distal end 146 and having a larger radius and appearing more shallow or flat towards the proximal end 144. It should be noted that any given cross-section of either the medial or lateral plates may include more than one radius. Accordingly, the inner surface may form an arc with a varying radius or may form more than one arc. The proximal end 144 has a rounded distal most edge and a bull-nosed leading edge that accommodates insertion along the bone structure. In addition, the width of the plate increases as the distance from the proximal end increases toward a maximum width region. Connection features 148a-c receive or connect with one of the axle 106, the pin 108, and the bone screw 110. In the embodiment shown, a side edge of the lateral plate, adjacent the connection features 148b, is wider than the plate at the distal and proximal ends 144, 146.

Figure 8:
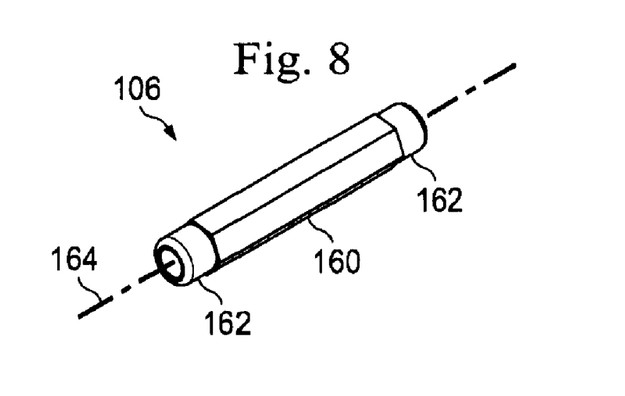
FIG. 8 is an illustration of an isometric view of an exemplary axle sleeve of the ankle distraction device of FIG. 1.

FIG. 8 shows the axle 106 in greater detail. The axle 106 includes a bone interfacing portion 160 and a plate interfacing portion 162 and has a longitudinal axis 164. In the embodiment shown, the axle 106 is a sleeve including a smooth inner surface that also acts as a drill guide or receives a drill guide when drilling though bone structure as will be further described below. Thus, in the embodiment shown, the axle 106 has first and second open ends and a substantially constant inner diameter.

The bone interfacing portion 160 is configured to pass through a bone on the opposing sides of the joint. In this embodiment, where the device 100 is an ankle distraction device, the axle 106 is configured to pass through the talus bone of the foot, below the tibia and fibula. Accordingly, the bone interfacing portion 160 extends through a passage in the talus from one plate 102, 104 to the other. In the embodiment shown, the exterior surface of the bone interfacing portion 160 is non-circular in cross-section. Because of this shape, the bone interfacing portion 160 is fixed relative to the talus in that it cannot rotate within the passage through the talus. In these embodiments, the non-circular outer surface is hex-shaped. However, other shapes also can be used, such as rectangular, triangular, and oval, among others. In the embodiment shown, the bone interfacing portion 160 has a cross-section sized greater than the opening of the connection features. Accordingly, the plates 102, 104 abut against both ends of the bone interfacing portion 160 over the plate interfacing portions 162. In some embodiments, the bone interfacing portion 160 is circular in cross-section rather than the hex shape shown to more easily maintain wear within acceptable levels. In addition, edges of the non-circular bone interfacing portion 160 may be rounded or circular in cross-section (as shown in the embodiment in FIG. 12) to reduce thrust bearing effects against the plate, thereby reducing a chance of wear on the plates where they meet the bone interfacing portion.

The plate interfacing portions 162 are located at either end of the bone interfacing portion 160. In the embodiment shown, these are cylindrically shaped, having a round cross-section and are configured to act as bearings with the plates 102, 104. More particularly, these receivable in the most-distal connection features 122e, 148c of the plates 102, 104 and are sized and shaped to rotate about the bearing longitudinal axis 164. When assembled with the plates, the plate interfacing portions 162 extend through the plates and the plates are adjacent to or abut against the sides of the bone interfacing portion 160. In some embodiments, a portion of the inner diameter of the axle 164 or a portion of the plate interfacing portions 162 is threaded to receive a locking bolt or nut to secure the axle 106 to the plates 102, 104. In some of these embodiments, the locking bolts or nuts include spherical heads that correspond to spherical countersinks of the connection features 122, 148. In other embodiments, the connection features on the plates comprise a captured spherical bushing into which the plate interfacing portions are placed or secured. Although shown as being cylindrically shaped, in other embodiments, the plate interfacing portions have a generally spherical or other shape. Such alternative plate interfacing portions may permit a wider range of plate alignment.

Like the axle 106, the pin 108, best seen in FIG. 1, extends from one plate to the other. This pin 108 however, is disposed through the second most distal connection feature 122d, 148b in each plate 102, 104. Accordingly, the pin 108 connects to the plates in the relatively wide areas of the plates, and in the embodiment shown, connects to the medial plate substantially at the deepest portion of the concave socket portion 128. The pin 108 may be a wire or shaft and may include a head at one end and be configured to receive a nut on the other, may thread onto a fixed thread in the plate, onto a captured spherical bushing, or have other arrangements. In some embodiments, the head and nut are spherical and received into a spherical socket or countersink at the connection features. The pin 108 is sized and configured to keep the plates from spreading apart, and in cooperation with the shoulder 130, may support a portion of the weight of the patient. It should be noted that although the device 100 is shown with a single pin 108, other embodiments accommodate and include more than one pin extending through the intermediate bone structure and connecting the medial and lateral plates.

Figures 9, 10:
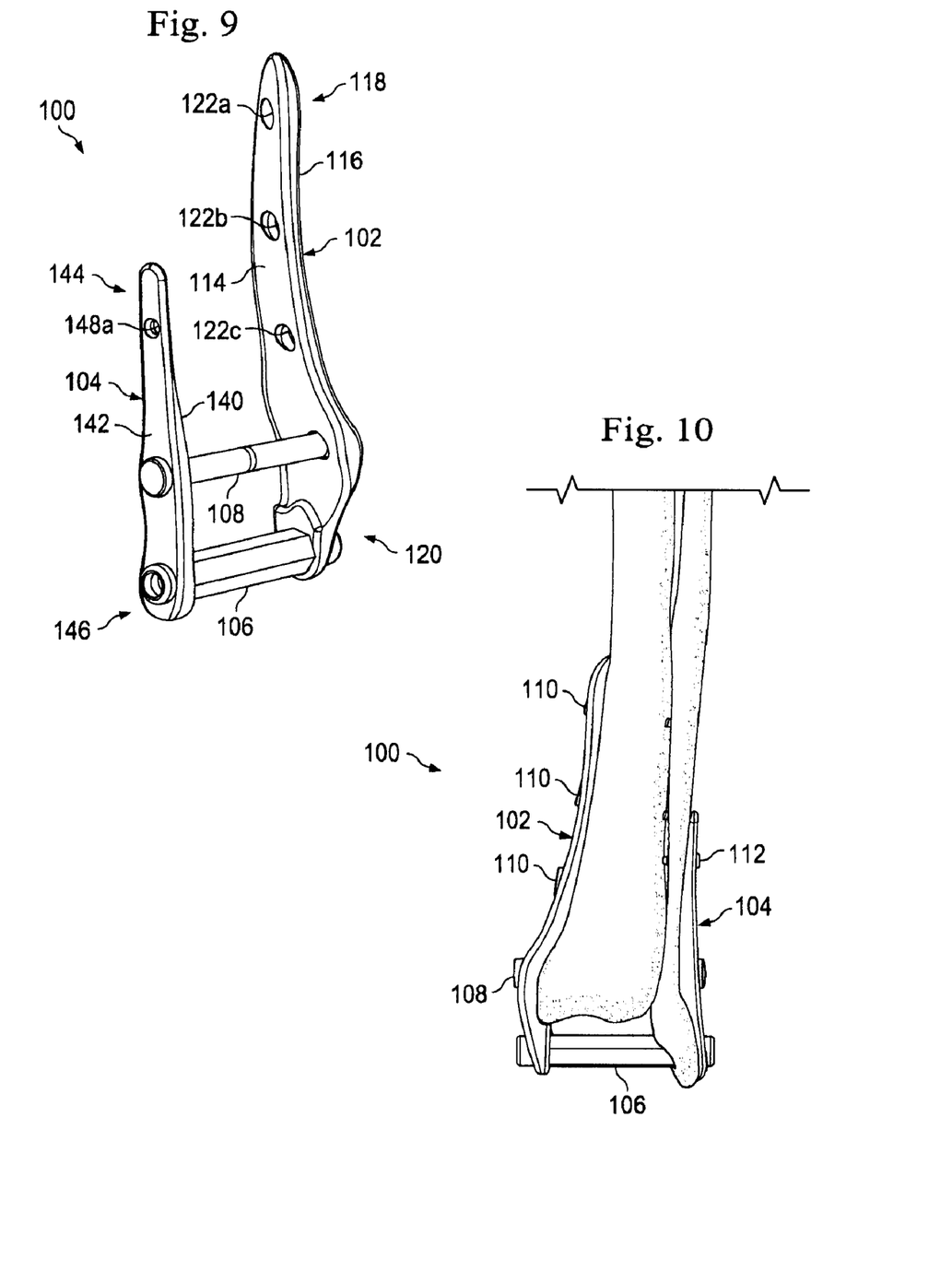
FIG. 9 is an illustration of an isometric view of the ankle distraction device of FIG. 1.
FIG. 10 is an illustration of a posterior view of the ankle distraction device attached to a tibia and fibula.

FIG. 9 shows the medial and lateral plates 102, 104 connected to each other by the axle 106 and pin 108. FIG. 10 shows a posterior view of the medial and lateral plates 102, 104 connected in place on the tibia and fibula respectively. In this embodiment, the distance between the connection features 122e and 122d on the medial plate 102 is different than the distance between the connection features 148c and 148b on the lateral plate 104. Accordingly, when the axle 106 and the pin 108 are both aligned in the respective connection features on the plates, they may be not parallel. Instead, the arrangement provides desired support while maintaining the pivot axis, defined by the axle 106, in a proper orientation.

As can be seen in FIG. 10, the tibia fits into the shoulder 130. This helps maintain the medial plate 102 in place and bears the weight of the patient. However, in some embodiments at least, a portion of the bearing weight of the patient is on the pin 108 extending through both the tibia and fibula rather than on the shoulder 130, helping maintain the integrity of the tibia end. The axle 106 passes below the tibia, but penetrates the fibula.

In use, the axle 106 aligns with the axis of the ankle joint. Articulating pivot motion can be obtained by pivoting the talus or foot about the joint. Because both the medial plate 102 and the lateral plate 104 connect with the axle 106, they are both sized and configured to extend beyond the tibia and past the ankle joint.

Figure 11:
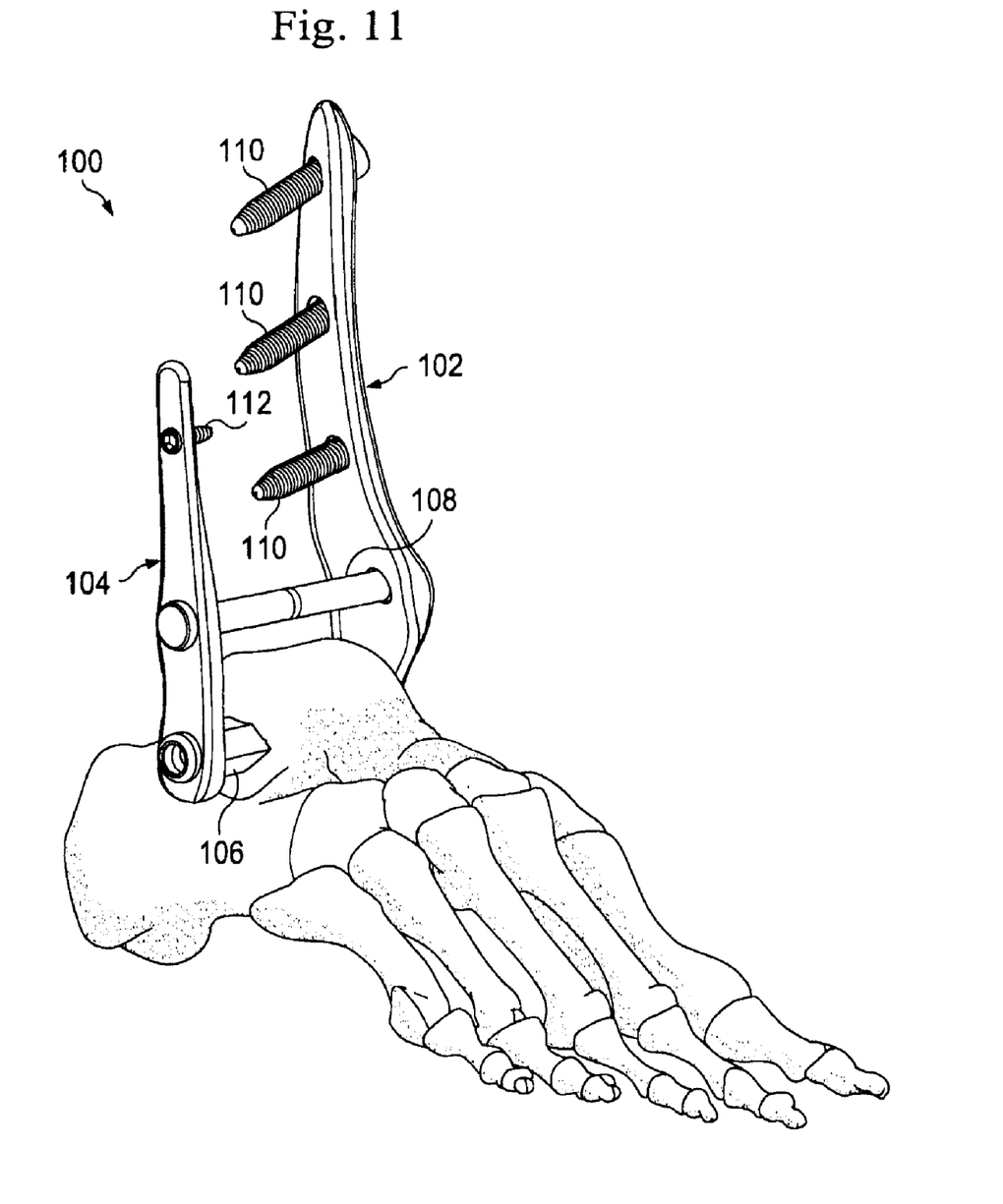
FIG. 11 is an illustration of an isometric view of the ankle distraction device attached to a bone structure of a foot.

FIG. 11 shows the bone structure of a patient's foot with the device 100 in place. Here, the axle 106 extends through the talus on either side of the foot. The bearing interface between the plate interfacing portion 162 and the plates 102,104 provides a bearing surface, such as a journal bearing surface, that allows the bearing, and thus the foot, connected to the bearing to pivot about the bearing axis. The bearing's splined bone interfacing portion 160 forces the bearing to pivot with the bone, instead of within it.

In other embodiments, the axle 106 includes an outer sleeve acting as a bushing and an inner sleeve or shaft that supports the outer sleeve coaxial with the joint axis. In these embodiments, the outer sleeve interfaces with and may be fixed to the lower bone structure, such as the talus, while the inner sleeve or shaft may be fixed to the plates. As the outer sleeve pivots about the inner sleeve, the talus likewise articulates about the joint axis.

In some alternative embodiments, each of the plates 102, 106 include a boss, such as a cylindrical boss, sized and shaped to fit within bores formed in the adjacent bone structures. For example, the bosses may fit within cylindrical bores in the tibia and fibula adjacent the plates. These bosses may bear the weight of the patient to maintain the joint in its distracted state. In other embodiments, the plates include thimble-like cups that extend below and are shaped to receive the ends of the bone structures, such as the ends of the tibia and fibula.

FIGS. 12-17 show another exemplary embodiment of a distraction device, referenced herein by the numeral 200. This embodiment is like the embodiment described above in many respects, but also includes a built-in or self-contained distraction capability. This capability may simplify surgical procedures for joint treatment as it is entirely contained and implantable within the body. It should be noted that any of the features in this disclosure may be included in any of the disclosed embodiments.

Figure 13:
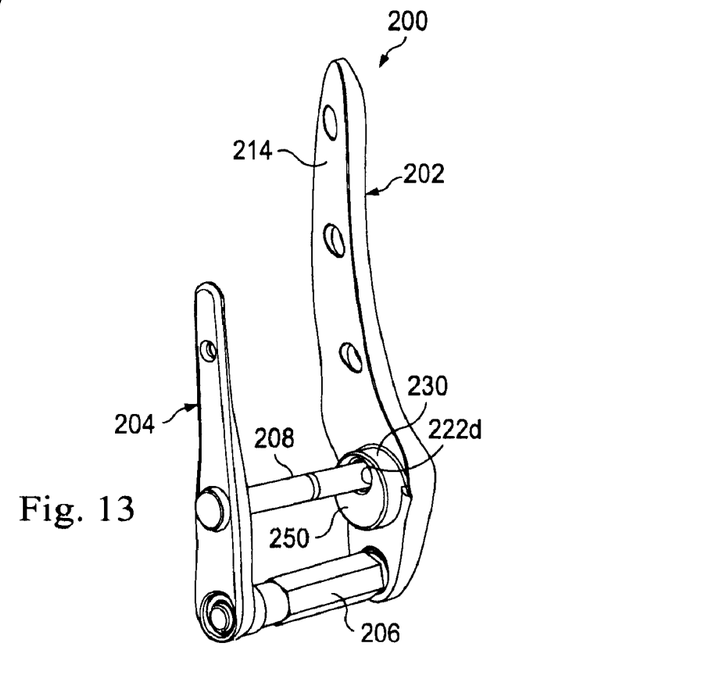

Similar to the device above, the device 200 includes a medial plate 202, a lateral plate 204, an axle 206, and a pin 208. Connection features in the plates receive bone screws, the axle 206, and the pin 208. In this embodiment, as best seen in FIG. 13, the medial plate 202 includes a cylindrical boss 250 as an offset bearing portion projecting from an inner facing side 214. The cylindrical boss 250 is disposed such that the connection feature 222d attaching the pin 208 extends therethrough. Like the pin 208, the cylindrical boss 250 is configured to bear weight of the patient applied by the adjacent bone structure. Here, the boss may be shaped to correspond to and fit within a bore formed in the medial side of the tibia. It supports longitudinal loads along the tibia and provides a more substantial cross-section for the acceptance of the pin 208. Accordingly, the inner surface of the plate 202 substantially conforms to the profile or outer surface of the bone structure while the boss 250 protrudes into the bone structure. The cylindrical side surface of the boss 250 forms a shoulder 230 that may bear at least a portion of the weight of the patient. Although described as a cylindrical boss, in other embodiments, the shape of the boss is non-cylindrical, but is shaped to a match a corresponding non-cylindrical cutout or bore in the adjacent bone structure. For example, the boss may be a half of a cylinder or semi-cylindrical, oval shaped, squared, squared with rounded corners, or have other shaped features.

Figure 12:
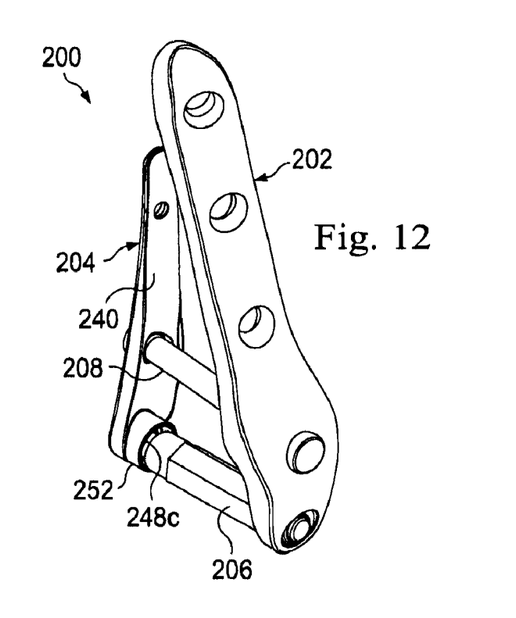
FIGS. 12 and 13 are illustrations of an isometric view of an exemplary ankle distraction device according to another aspect.

The lateral plate 204 also includes a cylindrical boss 252, best seen in FIG. 12, extending from its inner facing side 240. In this embodiment, instead of the boss being aligned adjacent the pin 208, the boss 252 is disposed to be adjacent the axle 206. Here, the cylindrical boss 252 is formed at the most-distal end 244 of the plate 204 and the cylindrical side surface of the boss 252 aligns with the most-distal end. Like the boss 250 on the medial plate 202, the boss 252 on the lateral plate 204 fits within a matching bore formed in the adjacent bone structure and may support applied weight.

In the embodiment shown, the connection feature 222d for receiving the pin 208 is formed non-concentrically with the medial plate boss 250. In contrast, the connection feature 248c for receiving the axle 206 is formed concentrically with the lateral plate boss 252. The actual location of the bosses and connection features may vary depending upon the joint and bone structure being treated.

Like the axle 106, the axle 206 permits the lower bone structure to articulate relative to the upper bone structure with an entirely self-contained, implantable articulation system. In this embodiment, between each plate 202, 204 and each end of the axle 206, the device 200 also includes a non-concentric cylindrical bushing 254 and a spherical bushing 256. These make up a self-contained distraction system implantable entirely within a patient.

The axle 206 includes a bone interfacing portion 260 and a plate interfacing portion 262 and extends along a longitudinal axis 264. Forming a part of the bone interfacing portion, this embodiment includes a non-circular portion 266 (shown as a splined portion in FIG. 14) and a cylindrical portion 268. When used at the ankle joint, the axle 206 extends through both the talus and the fibula as discussed above. The splined or non-circular portion 266 of the axle 206 is configured to extend only in the region interfacing with the talus, while the cylindrical portion 268 is configured to extend only in the region of the fibula. Accordingly, the splined portion does not extend from plate to plate, but extends within the range of about 50-85% of the distance between the plates. The remainder of the axle 206 between the plates has a smaller overall diameter or is formed with a circular cross section. As indicated above, this may reduce thrust bearing effects against the plate, thereby reducing a chance of wear on the plates where they meet the bone interfacing portion.

Figures 14, 15:
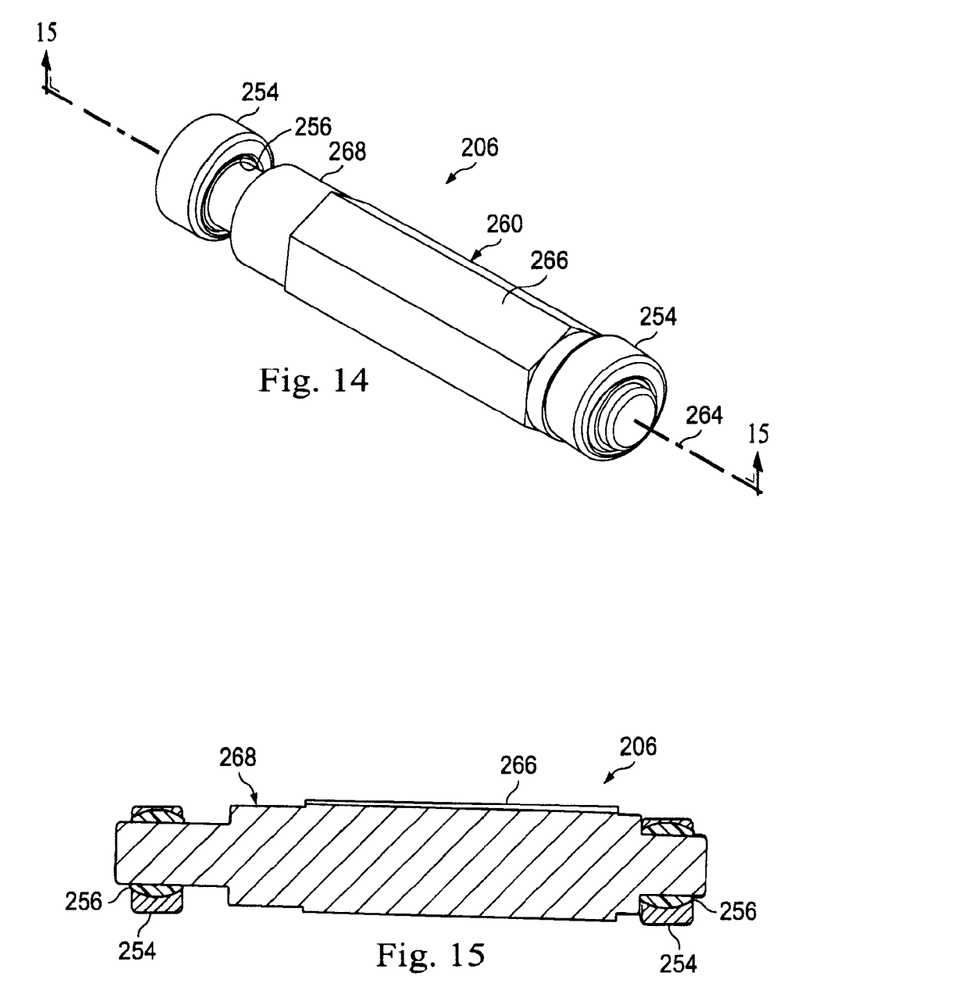
FIGS. 14-16 are illustrations of an exemplary axle with bushings according to the aspect of FIGS. 12 and 13.

In this embodiment, the plate interfacing portions 262 at each end are formed as cylindrical ends that mate with the bushings 254, 256 within the connection features on the plates. The spherical bushings 256 permit the axle to align with the connection features on each plate while the cylindrical bushings 254 can be rotated to distract the axle and plates.

Figure 16:
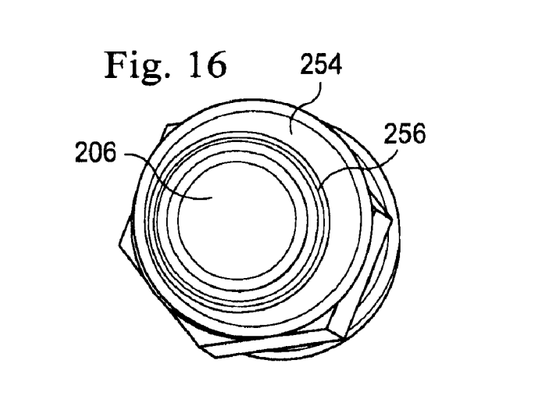

With reference to FIGS. 15 and 16, the non-concentric bushing 256 has an inner spherical surface that mates with the spherical bushing and an outer cylindrical surface that mates with the cylindrical connection feature in the plates. Because of its non-concentric shape, rotation of the cylindrical bushing 256 relative to the plate 202, 204 and the axle 206 displaces the axle relative to the plates. This self-contained, implantable distraction system may be used to distract the upper and lower bone portions, alleviating loading on the joint. Here, the plate is maintained in its original form with the axle providing the distraction.

Bushing rotation may be accomplished by any of a variety of contemplated processes. In some examples, the bushing includes one or more tool receiving features formed thereon for interfacing with a distraction tool. For example, in one embodiment, the bushing includes a plurality of receiving holes for receiving pins on the distraction tool. After inserting the pins into the receiving holes, rotation of the tool correspondingly rotates the bushing. In other embodiments, the bushing has a hex portion receivable in a hex socket. Additional processes and tools are contemplated.

Although distraction is obtained in this embodiment with a non-concentric bushing, it should be noted that distraction may be obtained in other ways as well. For example, some embodiments use a non-concentric spherical bushing, while in other embodiments, the axle itself has ends non-concentric with the bone interfacing portion 260. In embodiments not using bushings, such as the device 100, the plates may include spherical connection features and the axle 106 may include non-concentric ends or inner and outer non-concentric sleeves. Other embodiments employ axial distraction methods for plate distraction rather than axle distraction. For example, distraction systems as disclosed in U.S. Pat. Nos. 5,074,882 and 5,704,939, incorporated herein in their entirety by reference, may be employed in the plates to accommodate distraction.

It should be noted that in some embodiments, the device 200 is used without the non-concentric bushing. Accordingly, in such embodiments, joint distraction may be accomplished with conventional procedures, and the system 200 may maintain the joint in the distracted state.

Figure 17:
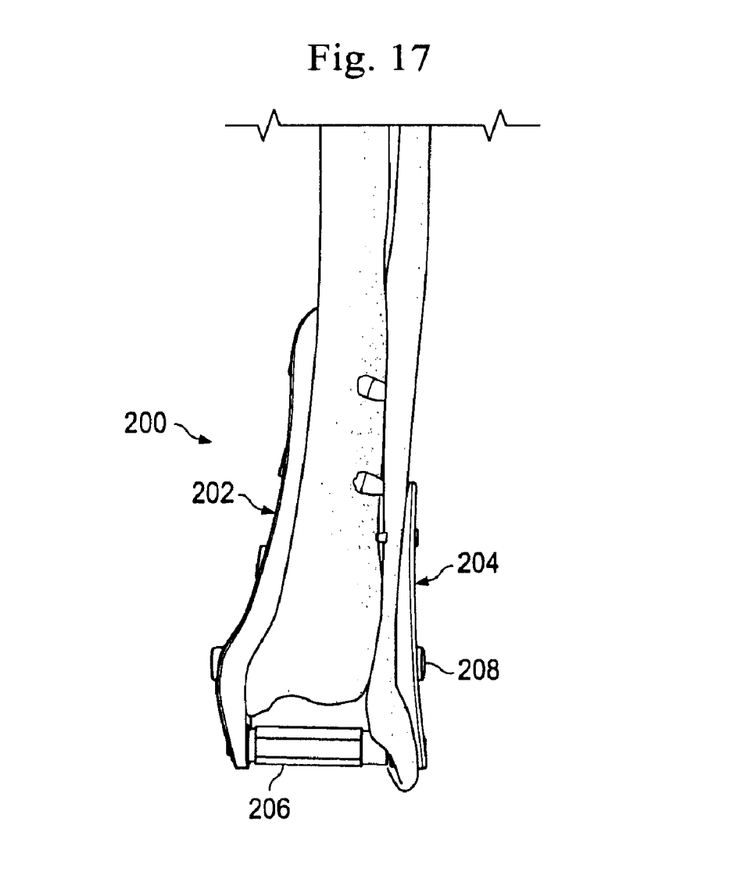
FIG. 17 is an illustration of a posterior view of the ankle distraction device of FIGS. 12 and 13 attached to a tibia and fibula.

FIG. 17 shows a posterior view of the medial and lateral plates 202, 204 connected in place on the tibia and fibula respectively. As can be seen, the boss 252 fits with a bore formed in the fibula and supports weight on the fibula. Although not explicitly shown, the tibia includes a bore that receives the medial plate boss to support weight applied on the tibia. The axle 106 passes below the tibia, but penetrates the fibula. In use, the axle 206 aligns with the axis of the ankle joint. Articulating pivot motion can be obtained by pivoting the talus or foot about the joint. Because both the medial and lateral plates 202, 204 connect with the axle 106, they are both sized and configured to extend beyond the ankle joint.

An exemplary procedure for implanting the devices 100, 200 is described below. If using an embodiment without a self-contained distraction system, the patient is placed in traction to distract the ankle joint using conventional methods known in the art. Then, the health care provider makes a small incision on both the lateral and medial side of the ankle to provide access to the joint. A passage through the talus along the axis of the joint provides a pivot axis for the joint in its distracted state. The provider then introduces the axle 106, 206 into the passage and through the talus. In some instances, where the axle has a non-cylindrical bone interfacing portion, the passage is formed having a non-cylindrical shape so that the bone passage interface matches and mates with the axle.

The axle 106, 206 acts as a journal bearing with the plates and is fixed relative to the talus through the use of the external shape of the bone interfacing portion 160, 260, such as the spline, or some other feature to prevent rotation within the talus. It should be noted that in some embodiments, the joint axis is anterior with respect to the calcaneotibial ligament and posterior with respect to the tibionavicular ligament.

A corresponding bore in the fibula, through which the bone interfacing portion 160, 260 passes, may be formed from the medial side utilizing a drill guide placed within the sleeve of the axle 106. Alternatively, the fibula bore is formed from its lateral side to align with the talus passage. In some embodiments using an axle like the axle 106, the fibula bore has a diameter greater than the bone interfacing portion 160 of the axle 106. This permits the axle 106 to be fixed relative to the talus, but to rotate relative to the fibula when in place. In other embodiments, using an axle like the axle 206, the fibula bore may have a diameter equal to or smaller than the bone interfacing portion 260 of the axle 206. In these embodiments, the non-splined portion may either not contact the inner surface of the fibula bore or may slidingly pivot within the fibula bore.

The health care provider inserts the lateral plate 104, 204 up through the incision along side the fibula and places the plate so that the most distal hole, connection feature 148c in this embodiment, aligns with the axis of the axle 106, 206. The rounded proximal most edge and a bull-nosed leading edge assists with insertion along the bone structure while minimizing tissue damage to the epidermis and other tissue adjacent the ankle. The cylindrical boss, if provided, fits within the bore in the fibula in a manner to support applied weight from the fibula. This plate 104, 204 may then be secured with bone screws, such as spherically headed, locking screws, non-locking screws, or other screws or anchors, through the connection feature 148*a* and/or other connection features if provided. The first and second distal most connection features on the lateral plate 104, 204 are reserved for the use of the through pin 108, 208 and the axle 106, 206.

The axle 106, 206 is then passed into the fibula and the plate interfacing portion is inserted through the proximal most connection feature 148*c* into the lateral plate 104, 204. In embodiments employing bushings 254, 256, the plate interfacing portions fit into the bushings.

In some instances, a provider forms the receiving bone structure to accommodate the features of the medial plate 102, 202. For example, using a plate with the cylindrical boss 250, a corresponding bore is formed into the tibia. The provider then inserts the tibia plate or medial plate 102, 202 up through the medial incision along side the tibia. Again, the rounded proximal most edge and a bull-nosed leading edge assists with insertion along the bone structure while minimizing tissue damage to the epidermis and other tissue adjacent the ankle. The plate 102, 202, may be placed so that the boss fits within corresponding formed features in the bone. The plate 102, 202 fits over the head of the axle 106, 206 and is secured with bone screws 110 in the most proximal connection features. In some embodiments, a nut is then placed over the head of the axle to secure the axle to the tibia plate or medial plate. This nut, like the pin 108, 208, helps prevent the plates from splaying or separating and becoming disengaged from the axle's bearing plate interfacing portions. Other arrangements may be utilized to maintain the axle in the connection features, including cotter pins, formed shoulders in any of the plate, the axle, or bushings. Other methods also may be utilized.

With both plates now secured to the tibia and fibula respectively, and the axle in place through the talus and fibula, the pin 108, 208 is ready for attachment. Using fluoroscopy, a k wire is inserted through the second most distal connection feature on either of the plates in order find the corresponding proximal connection feature in the other. A cannulated drill is then used to drill the pinhole over the wire between the two plates. The pin 108, 208 is inserted and secured with a spherical headed nut. In some embodiments, the pin is threaded into a captured spherical bushing within the plate and can be inserted from either side. In others, it is threaded directly into the plate. Other steps, depending on the arrangement of the plates, are contemplated. It should be noted that the steps may be performed in orders other than that described herein.

Devices having self-contained distraction features may now be used to distract the upper and lower bone portions. In one embodiment, the non-concentric cylindrical bushing may be accessed and rotated with a distraction tool by connecting the tool to the bushing 254, and rotating the tool and bushing. The non-concentric bushing shape moves the axle center of axis from its first location to a second location different than the first location. Accordingly, the shaft can be moved either up or down along the plates by rotating the bushing. The device may be locked in its distracted state using conventional locking systems. For example, a pin may fit within keyed slots to restrict further rotation. Distracting the device removes loading from the joint cartilage, thereby permitting it to strengthen and heal, alleviating pain. During recovery, the axle permits the foot to articulate with the axle relative to the upper bone structure.

Although described as plates that interface against the medial and lateral sides of a bone structure, in alternative embodiments, the medial and lateral plates are intermedullary devices insertable within the canal of the adjacent bone structure.

It should be noted that in some embodiments, slots, openings, or other features may be included in the plates or other components to accommodate ligaments about the joint.

Applicants note that the use of directional terms herein, such as upper, lower, lateral, and others are merely exemplary, and may encompass other directions, such as the device being on its side, unless so indicated. Although several selected embodiments have been illustrated and described in detail, it will be understood that they are exemplary, and that a variety of substitutions and alterations are possible without departing from the spirit and scope of the present invention, as defined by the following claims.

We claim:

1. A treatment method for maintaining a first bone structure in a distracted state, comprising:
   creating a first passage through a talus substantially along a pivot axis of the ankle joint;
   inserting an axle through the first passage, the axle including structural features that prevent relative rotation of the axle relative to the talus;
   implanting a fibula bone plate in contact with and adjacent to the lateral side of the fibula such that a connection feature in the fibula bone plate aligns with the axis of the axle;
   connecting the axle to the fibula bone plate to provide articulating movement of the talus with the axle relative to the fibula;
   implanting a tibia bone plate in contact with and adjacent to the medial side of the tibia such that a connection feature in the tibia bone plate aligns with the axis of the axle;
   connecting the axle to the tibia bone plate to provide articulating movement of the talus with the axle relative to the tibia;
   creating a second passage through both the tibia and fibula that aligns with a connection feature on each of the fibula and tibia plates;
   implanting a pin through the second passage that connects to both the fibular fibula and tibia bone plates.

2. The method of claim 1, wherein implanting the fibula and tibia bone plates is accomplished percutaneously.

3. The method of claim 1, wherein implanting the pin comprises:
   passing a K wire through the second most distal connection features on the first and second bone plates; and
   drilling the second passage over the K wire; and
   passing the pin through the second passage and connecting the pin to the first and second plates.

4. The method of claim 1, further comprising driving spherically headed bone screws though the plates so that spherical heads rest in spherical countersinks formed in the plates.

5. The method of claim 1, wherein implanting the tibia plate includes orienting a distal end of the tibia into a recessed shoulder portion shaped to receive a portion of the end of the tibia.

6. The method of claim 1, comprising drilling a passage in the fibula using a drill guide in the axle.

7. The method of claim 1, wherein implanting includes percutaneously sliding one of the fibula bone plate and the tibia bone plate along the respective fibula or tibia under the epidermis.

8. The method of claim 1, further comprising forming a bore in the tibia and wherein implanting a tibia bone plate comprises inserting a boss formed on the inner surface of the tibia bone plate into the bore such that the boss carries loading applied by the tibia.

9. The method of claim 1, including distracting the tibia and the talus using a self-contained, fully implantable distraction system.

10. The method of claim 9, wherein distracting includes rotating a non-concentric bushing.

* * * * *